(12) United States Patent
Gokaraju et al.

(10) Patent No.: US 7,893,263 B2
(45) Date of Patent: *Feb. 22, 2011

(54) STRUCTURAL ANALOGS OF COROSOLIC ACID HAVING ANTI-DIABETIC AND ANTI-INFLAMMATORY PROPERTIES

(75) Inventors: Ganga Raju Gokaraju, Andhra Pradesh (IN); Rama Raju Gokaraju, Andhra Pradesh (IN); Venkata Subbaraju Gottumukkala, Andhra Pradesh (IN); Trimurtulu Golakoti, Andhra Pradesh (IN); Venkateswarlu Somepalli, Andhra Pradesh (IN); Venkateswara Rao Chirravuri, Andhra Pradesh (IN)

(73) Assignee: Laila Nutraceuticals, Andhra Pradesh (IN)

( * ) Notice: Subject to any disclaimer, the term of this patent is extended or adjusted under 35 U.S.C. 154(b) by 257 days.

This patent is subject to a terminal disclaimer.

(21) Appl. No.: 10/543,387

(22) PCT Filed: Jul. 8, 2004

(86) PCT No.: PCT/IN2004/000202

§ 371 (c)(1),
(2), (4) Date: Jul. 26, 2005

(87) PCT Pub. No.: WO2006/006178

PCT Pub. Date: Jan. 19, 2006

(65) Prior Publication Data

US 2007/0167521 A1 Jul. 19, 2007

(51) Int. Cl.
C07C 45/00 (2006.01)
C07C 47/00 (2006.01)
C07C 233/00 (2006.01)
C07C 235/00 (2006.01)
C07D 211/78 (2006.01)
C07D 211/90 (2006.01)
C07D 241/04 (2006.01)
C07D 295/00 (2006.01)

(52) U.S. Cl. ............... 544/380; 546/322; 564/188; 568/445

(58) Field of Classification Search ............... 544/380; 546/322; 564/188; 568/445
See application file for complete search history.

(56) References Cited

U.S. PATENT DOCUMENTS

| 5,064,823 | A  | * | 11/1991 | Lee et al. ............... 514/198 |
| 6,369,101 | B1 | * | 4/2002  | Carlson ............... 514/468 |
| 6,572,897 | B1 | * | 6/2003  | Gorsek ............... 424/655 |
| 6,689,767 | B2 | * | 2/2004  | Krasutsky et al. ............ 514/169 |
| 6,903,136 | B2 | * | 6/2005  | Miller et al. ............... 514/556 |
| 6,974,801 | B2 | * | 12/2005 | Honda et al. ............... 514/25 |
| 7,071,229 | B2 | * | 7/2006  | Takayama et al. ............ 514/559 |
| 7,195,790 | B2 | * | 3/2007  | Zhang et al. ............... 424/764 |
| 2002/0010168 | A1 | * | 1/2002 | Ammon et al. ............. 514/198 |
| 2003/0165581 | A1 | * | 9/2003 | Wang et al. ............... 424/725 |
| 2003/0199581 | A1 | * | 10/2003 | Seligson et al. ............. 514/548 |
| 2004/0166181 | A1 | * | 8/2004 | Hegenauer et al. .......... 424/757 |

OTHER PUBLICATIONS

Abe et al. Indole alkaloids from leaves of Astonia macrophylia in Thailand. Phyrochemistry. 1994;35(1):249-252, abstract only.*
Pinto et al. Cannabinoid receptor binding and agonist activity of amides and esters of arachidonic acid. Molecular Pharmacology. 1994. 46(3):516-522, abstract only.*
Nishimura et al. Activity-guided isolation of triterpenoid acyl CoA cholesteryl acyl transferase (ACAT) inhibitors from Llex kudincha. J Nat Prod. 1999. 62(7):1061-4, abstract only.*
Nomura et al. Metabolism of vasodilator 4-(3,4,5-trimethoxycin-namoyl)-1-(1-pyrrolidinyl) carbonylmethylpiperazine (cinepazide): isolated and identification of metabolites in the rat and man. J Pharmacobiodyn. 1980;3(6):281-9, abstract only.*
Ikuta et al, "Ursane- and Oleanane-Type Triterpenes from Ternstroemia gymnanthera Callus Tissues", J. Nat. Prod., 66, pp. 1051-1054 (2003).*
Garcia-Granados et al, "Epoxides, Cyclic SUlfites, and Sulfate from Natural Pentacyclic Triterpenoids: Theoretical Calculations and Chemical Transformations", J. Org. Chem., 68, pp. 4833-4844 (2003).*
Database CAPLUS on STN, AN:1984:171519, Talapatra et al., "Lagerenyl acetate and lagerenol, tow tetracyclic triterpenoids with the cycloartane skeleton from Lagerstroemia lancasteri." Phytochemistry. 1983, vol. 22, No. 11, pp. 2559-2562, see abstract.
Database CAPLUS on STN, AN:1977:458441, Ogura et al, "Potential anticancer agents IV. Constituents of Jacaranda caucana Pittier Bignoniaceae)."Lloydia, 1977, vol. 40, No. 2, pp. 157-168, see Abstract.

* cited by examiner

*Primary Examiner*—Sharmila Gollamudi Landau
*Assistant Examiner*—Barbara Frazier
(74) *Attorney, Agent, or Firm*—Rader, Fishman & Grauer PLLC

(57) ABSTRACT

This invention relates to novel corosolic acid analogs of the formula I, wherein $R_1$, $R_2$, $R_3$, $R_4$ and $R_5$ are described herein. These compounds exhibit good hypoglycemic and 5-lipoxygenase inhibitory activities. They also inhibit tumour growth. Pharmaceutical compositions containing known adjutants and the title compounds are also within the scope of this invention.

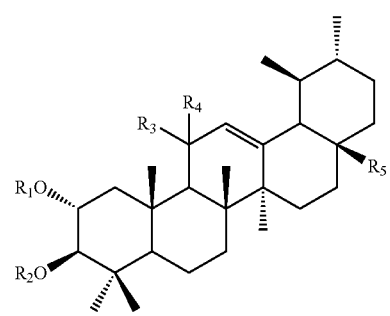

9 Claims, No Drawings

STRUCTURAL ANALOGS OF COROSOLIC ACID HAVING ANTI-DIABETIC AND ANTI-INFLAMMATORY PROPERTIES

This invention relates to novel structural analogs of corosolic acid having anti-diabetic and anti-inflammatory properties. These compounds are found to exhibit potent hypoglycemic, 5-lipoxygenase inhibitory and antitumor activities.

TECHNICAL FIELD

Diabetes is perceived as a disorder of metabolism, where body's natural ability to utilize food that has been broken down by digestion is vitiated. The body utilizes glucose, a major metabolic product from food, for energy and for cell growth. Glucose disperses throughout the body through the blood stream and enters cells with the help of a hormone called insulin. Insulin is produced by pancreas, a large gland beneath the stomach. In people with diabetes mellitus, either the pancreas does not produce enough insulin to move the glucose into the cells or the cells do not respond to the insulin, even though plenty is produced (Reaven, G. M., Role of insulin resistance in human disease; *Diabetes*, 1998, 37, 1595-1607). As a result of this impairment, glucose builds up in the blood stream and excreted out of the body without ever having been used as fuel.

Untreated diabetes can lead to very serious chronic problems, including heart disease, kidney failure, blindness, nerve damage and amputations (Porte, D. et al., *Science*, 1996, 27, 699-700). Many experts believe that diabetes, cardiovascular disease and obesity all have a common factor linked by a condition called insulin resistance also known as Syndrome X (Bagchi, D., Syndrome X, The Diabetes, CVD and Obesity link, Health Products Business, June 2001, 62). But with proper management, the risk of such problems can be greatly reduced. The management plan depends on the type of diabetes: insulin-dependent diabetes mellitus (IDDM) or noninsulin-dependent diabetes mellitus (NIDDM).

BACKGROUND ART

There are a number of agents currently available in the market for diabetes management, which belongs to various structural types. For example, thiazolidinediones, sulfonyl ureas, alpha-glucosidase inhibitors and biguanides are some of the drug types currently available in the market. According to the American Diabetes Association, diabetes mellitus is estimated to effect 6% of the world population and the recent studies indicate that the number of diabetic patients could rise to 300 million by 2025. Worldwide sales of antidiabetic drugs reached 10 billion US dollars in 2002. Oral antidiabetics accounted for 63% of these sales and glucophase (metformin) was the leading product. With rising number of people suffering from diabetes worldwide, the market for diabetes medications could exceed $20 billion by 2006. In the natural products arena, a handful of herbal medications were proven to be effective against this terrible menace. For example, Fenugreek (*Trigonella foenumgraecum*), Gymnema (*Gymnema sylvestre*), Jamun/Jambolan (*Syzygium cumini*), Bitter melon/Karela (*Momordica charantia*) and Banaba (*Lagerstroemia speciosa*) are some of the products known to show hypoglycemic activity. Natural antidiabetic treatments have gained popularity in the recent years because of their proven safety from long history of usage in traditional medicine and also present usage in herbal treatments. Banaba, *Lagerstroemia speciosa* L, has gotten the worldwide attention in the past few years as organic insulin. It is widely distributed in Philippines, as well as in Malaysia, South China and tropical Australia. Corosolic acid or colosolic acid (2α-hydroxyursolic acid, CAS No. 4547-24-4), a triterpenoid compound isolated from the banaba extract was found to be responsible for the antidiabetic activity. Banaba has long been recognized for the treatment of diabetes and also for maintenance of low blood pressure and improved kidney function in Philippines and other East Asian countries. Clinical studies confirmed the hypoglycemic effects of corosolic acid (Judy, W. V. et. al., *J. Ethnopharmacol.*, 2003, 87(1), 115-7). Indian species of Lagerstroemia (*Lagerstroemia parviflora, Lagerstroemia indica, Lagerstroemia speciosa*, etc), which grows along east coast from Orissa to West Bengal, also produce corosolic acid. Matsuyama, U.S. Pat. No. 6,485,760 (2002) described the blood sugar lowering effect of *Lagerstroemia* extract.

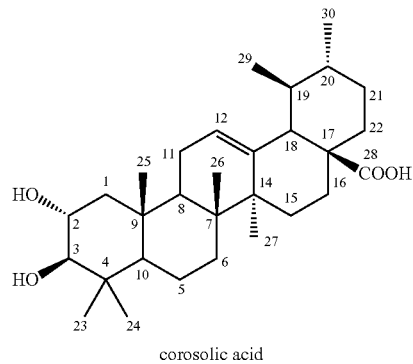

corosolic acid

Presently, there has been a tremendous surge in the demand for non-steroidal, plant based anti-inflammatory agents. 5-Lipoxygenase is the key enzyme for the biosynthesis of leukotrienes and 5(S)-HETE, the important mediators, for inflammatory, allergic and obstructive process, from arachidonic acid. 5-Lipoxygenase is the target enzyme for identifying inhibitors, which have the potential to cope with a variety of inflammations and hypersensitivity-based human diseases including asthma, arthritis, bowl diseases such as ulcerative colitis and circulatory disorders such as shock and ischaemia. Scientists around the world have invested major effort during the last ten years, in identifying 5-lipoxygenase inhibitors from plant sources. Gum resin of *Boswellia* species known as Indian frankincense has been used as an anti-inflammatory agent in traditional Ayurvedic Medicine in India. The source of anti-inflammatory actions has been attributed to boswellic acids (Safayhi, H., et al., *Planta Medica*, 1997, 63, 487-493 and *J. Pharmacol. Exp. Ther.*, 1992, 261, 1143-46, both the journals published from USA), a group of triterpene acids isolated from the *Boswellia* resin (Padhy, R. S., et al., *Indian J. Chem.*, 1978, 16B, 176-178). During our search for new anti-inflammatory agents, we have observed, to the best of our knowledge for the first time that corosolic acid is a potential inhibitor of 5-LOX. The inhibitory activity was found to be on par with 3-O-acetyl-11-keto-β-boswellic acid (AKBA).

The olenane and ursane triterpenoids also gained prominence recently for their antiproliferative actions. As 5-lipoxygenase (5-LOX) is the first enzyme in the metabolic pathway leading to the formation of leukotrienes and eicosanoids that are important in carcinogenesis process, inhibitors of 5-LOX may thus have profound influence on the growth and apoptosis of various cancer lines (Yong S. Park, et. al., *Planta Medica*, 2002, 68, 397-401). Boswellic acids, for example inhibited several leukemia cell lines in vitro and inhibited melanoma growth and induced apoptosis (Hostanska, K., et. al., *Anticancer Res.*, 2002, 22(5), 2853-62). The acetyl boswellic acids were found to be unique class of dual inhibitors of human topoisomerages I and II α (Syrovets, T. et. al., *Mol. Pharmacol.*, 2000, 58(1), 71-81). A number of oleanane and ursane tripenoids were found to be powerful inhibitors of nitric oxide production in macrophases, which can be correlated to their cancer chemoprevention activity (Honda, T. et. al., *J. Med. Chem.*, 2000, 43, 1866-77). Corosolic acid, which has the gross structure very similar to AKBA and other ursane derivatives, may thus hold promise as an antitumor agent.

OBJECTS OF THE INVENTION

The present invention was aimed at producing novel analogs of corosolic acid for structure-activity relationship studies. The main objective was to make analogs with enhanced water solubility and increased hypoglycemic activity. The functional groups that can be expended to make new analogs are carboxyl group, trisubstituted double bond and vicinal diol. The hydroxyl groups found utility to couple with moieties like natural acids and aminoacids, which not only improves water solubility but also presumed to enhance the biological recognition to the parent compound in the transport process.

The acid function was utilized to attach highly polar amine moieties through an amide linkage. The same group can also be utilized to make ester compounds by reacting with alcohols or halides. The lower alkyl esters can be reduced with LAH (lithium aluminum hydride) to introduce an additional alcohol group as depicted in structure 23. Oxidizing agents suitable for allylic oxidation, such as chromium trioxide can be utilized to generate 11-ketocorosolic acid compounds. Allylic oxidation using NBS (N-bromosucinimide) however yielded a lactone 26. The acylation transformation can be controlled to yield monoacylated compounds or diacylated compound by limiting the quantities of acylating agent. The general strategy to attach amino acid unit was coupling of BOC (tert-butoxycarbonyl) protected amino acids like glycine and alanine etc. to corosolic acid using DCC (1,3-dicyclohexylcarbodiimide), DMAP [4-(dimethylamino)-pyridine] followed by deprotection of BOC group using HCl/dioxane to yield glycyl and alanyl derivatives, respectively, of corosolic acid.

SUMMARY OF THE INVENTION

This invention relates to a novel structural analogs of corosolic acid having the general formula I

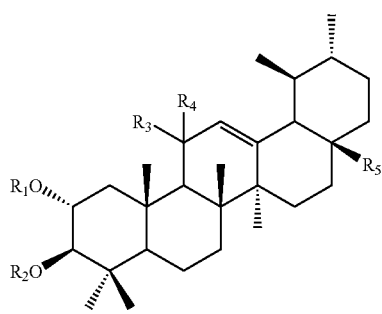

I wherein $R_1$, $R_2$, $R_3$, $R_4$ and $R_5$ are as indicated below in each of said analogs:

1. $R_1=COCH_3$, $R_2=R_3=R_4=H$, $R_5=COOH$ or $R_1=R_3=R_4=H$, $R_2=COCH_3$, $R_5=COOH$
2. $R_1=R_2=COCH_3$, $R_3=R_4=H$, $R_5=COOH$
3. $R_1=COC_5H_4N$, $R_2=R_3=R_4=H$, $R_5=COOH$
4. $R_1=COCH_2NH_2 \cdot HCl$, $R_2=R_3=R_4=H$, $R_5=COOH$
5. $R_1=COCH(CH_3)NH_2 \cdot HCl$, $R_2=R_3=R_4=H$, $R_5=COOH$
6. $R_1=COCH:CHC_6H_2(OCH_3)_3$, $R_2=R_3=R_4=H$, $R_5=COOCH_3$
7. $R_1$ & $R_2=SO_2$, $R_3=R_4=H$, $R_5=COOH$
8. $R_1=R_2=R_3=R_4=H$, $R_5=CONH_2$
9. $R_1=R_2=R_3=R_4=H$, $R_5=CONHC_6H_5$
10. $R_1=R_2=R_3=R_4=H$, $R_5=CONHCH_2CH_2NH_2$
11. $R_1=R_2=R_3=R_4=H$, $R_5=CON(CH_2CH_2)_2NH$
12. $R_1=R_2=R_3=R_4=H$, $R_5=CONHCH_2CH_2OH$
13. $R_1=R_2=R_3=R_4=H$, $R_5=COOCH_3$
14. $R_1=R_2=COCH_3$, $R_3=R_4=H$, $R_5=COOCH_3$
15. $R_1=R_2=H$, $R_3$ & $R_4=O$, $R_5=COOCH_3$
16. $R_1=R_2=COCH_3$, $R_3$ & $R_4=O$, $R_5=COOCH_3$
17. $R_1=R_2=H$, $R_3$ & $R_4=O$, $R_5=COOH$
18. $R_1=R_2=COCH_3$, $R_3$ & $R_4=O$, $R_5=COOH$
19. $R_1$ & $R_2=SO_2$, $R_3$ & $R_4=O$, $R_5=COOH$
20. $R_1=R_2=H$, $R_3$ & $R_4=O$, $R_5=CONH_2$
21. $R_1=R_2=R_3=H$, $R_4=OH$, $R_5=CONH_2$
22. $R_1=R_2=R_3=H$, $R_4=OH$, $R_5=COOCH_3$
23. $R_1=R_2=R_3=R_4=H$, $R_5=CH_2OH$
24. $R_1=R_2=R_3=R_4=H$, $R_5=CHO$
25. $R_1=R_2=R_3=R_4=H$, $R_5=COOCOC_6H_2(OCH_3)_3$
26. $R_1=R_2=R_3=H$, $R_4$ & $R_5=OCO$

BRIEF DISCLOSURE OF THE INVENTION

Identification of corosolic acid analogs having the above substituents and establishing their potent antidiabetic and anti-inflammatory action have been achieved by the applicants.

The corosolic acid (purity >95%) used in this study was obtained from the leaves of *Lagerstroemia speciosa*, using solvent extraction, chromatography over silica gel column and crystallization.

A further aspect of the present invention is a pharmaceutical formulation comprising a compound as described above in a pharmaceutically acceptable carrier (e.g., an aqueous or a non aqueous carrier).

A still further aspect of the present invention is a method of treating diabetes, comprising administering to a human or animal subject in need thereof a treatment effective amount (e.g., an amount effective to treat, slow the progression of, etc.) of a compound as described above.

The pharmaceutical compositions of the "compound" as used herein, includes the pharmaceutically acceptable salts of the compound. Pharmaceutically acceptable salts are salts that retain the desired biological activity of the parent compound and do not impart undesired toxicological effects. Examples of such salts are (a) base addition salts formed from metal hydroxides, $NH_4OH$, alkyl amines, pharmaceutically useful amine compounds etc. (b) acid addition salts formed with inorganic acids, for example hydrochloric acid, hydrobromic acid, sulfuric acid, phosphoric acid etc. on amine compounds represented by the formula I.

Active compounds of the present invention may be produced by the procedures described herein or variations thereof, which will be apparent to those skilled in the art. The intermediates useful for producing the compounds of the formula I, described herein are also an aspect of the present invention, as are methods useful for producing such intermediates and active compounds.

DESCRIPTION OF PREFERRED EMBODIMENTS

The present invention is explained in greater detail in the following non-limiting examples.

Example 1

2-O-Acetylcorosolic acid and 3-O-acetylcorosolic acid (1): To an ice cold solution of corosolic acid (500 mg, 1.06 mmol) in pyridine (0.75 mL, 9.7 mmol) was added slowly acetic anhydride (0.1 mL) and continued the stirring for 2 h. The mixture was poured into crushed ice and vigorously stirred. The solid was filtered, washed with water, dried and subjected to silica gel column chromatography using hexane-ethyl acetate (10%) mixture as eluent to furnish a white solid (220 mg); IR (KBr): 3434, 2927, 2863, 1722, 1695, 1456, 1256, 1030 cm$^{-1}$; It is a mixture of 3-O-acetyl and 2-O-acetyl derivatives in the ratio 1:2.7. NMR data corresponds to major product (2-O-acetyl derivative); $^1$H NMR (400 MHz, CDCl$_3$) δ 0.78 (3H, s, CH$_3$), 0.84 (3H, d, J=6.0 Hz, CH$_3$), 0.86 (6H, s, 2×CH$_3$), 0.95 (3H, d, J=4.8 Hz, CH$_3$), 1.06 (3H, s, CH$_3$), 1.08 (3H, s, CH$_3$), 2.06 (3H, s, —COCH$_3$), 2.20 (1H, d, J=11.3 Hz, H-18), 3.20 (1H, d, J=10.0 Hz, H-3), 4.92-4.98 (1H, m, H-2), 5.24 (1H, br s, H-12); NMR data corresponds to minor product (3-O-acetyl derivative): 2.14 (s, —COCH$_3$), 3.78-3.82 (m, H-2), 4.50 (d, J=10.0 Hz, H-3), 5.24 (br s, H-12); LCMS (negative ion mode): m/z 513 (M−H)$^-$.

3-O-Acetylcorosolic acid: IR (KBr): 3442, 2933, 2869, 1729, 1696, 1629, 1456, 1374, 1253, 1038 cm$^{-1}$; LCMS (negative ion mode): m/z 513 (M−H)$^-$.

Example 2

2,3-Di-O-acetylcorosolic acid (2): To a solution of corosolic acid (800 mg) in pyridine (5 mL) was added acetic anhydride (5 mL) and kept at rt for 16 h. The reaction mixture was worked up under the conditions noted in example 1, to give the diacetate, 2 (650 mg, 69%), m.p. 236-240° C.; IR (KBr): 3448, 2944, 2873, 1743, 1698, 1455, 1371, 1250, 1038, 962 cm$^{-1}$; $^1$H NMR (400 MHz, CDCl$_3$) δ 0.77 (3H, s, CH$_3$), 0.85 (3H, d, J=6.3 Hz, CH$_3$), 0.90 (6H, s, 2×CH$_3$), 0.95 (3H, d, J=5.9 Hz, CH$_3$), 1.07 (6H, s, 2×CH$_3$), 1.97 (3H, s, —COCH$_3$), 2.05 (3H, s, —COCH$_3$), 2.19 (1H, d, J=11.2 Hz, H-18), 4.75 (1H, d, J=10.3 Hz, H-3), 5.07-5.13 (1H, m, H-2), 5.24 (1H, br s, H-12); LCMS (negative ion mode): m/z 555 (M−H)$^-$.

Example 3

2-O-Nicotinoylcorosolic acid (3): To a mixture of corosolic acid (250 mg, 0.53 mmol), nicotinic acid (200 mg, 1.62 mmol) and DMAP (catalytic) in acetonitrile (50 mL) was added DCC (400 mg, 1.94 mmol) and stirred at rt for 24 h. The solids were filtered off and the solvent was evaporated. The residue was chromatographed over silica gel column using chloroform-methanol (20%) as eluent to furnish 2-O-nicotinoylcorosolic acid (33 mg, 11%), which was crystallised from chloroform-hexane, m.p. 212-216° C.; IR (KBr): 3434, 2928, 2871, 1722, 1594, 1456, 1288, 1132, 955 cm$^{-1}$; $^1$H NMR (400 MHz, CDCl$_3$) δ 0.81 (3H, s, CH$_3$), 0.84 (3H, d, J=6.3 Hz, CH$_3$), 0.92 (3H, s, CH$_3$), 0.95 (3H, d, J=6.3 Hz, CH$_3$), 1.11 (6H, s, 2×CH$_3$), 1.12 (3H, s, CH$_3$), 3.39 (1H, d, J=9.9 Hz, H-3), 5.24-5.27 (1H, br s, H-12), 7.37-7.41 (1H, m, Ar—H), 8.29 (1H, d, J=7.7 Hz, Ar—H), 8.78 (1H, d, J=3.5 Hz, Ar—H), 9.22 (1H, s, Ar—H); LCMS (negative ion mode): m/z 576 (M−H)$^-$.

Example 4

2-O-Glycylcorosolic acid hydrochloride (4): A mixture of corosolic acid (200 mg, 0.42 mmol), BOC protected glycine (82 mg, 0.47 mmol) and DMAP (30 mg) in dry dioxane (2 mL) at 0° C. was treated with DCC (130 mg, 0.63 mmol) under vigorous stirring. After 3 h, the reaction mixture was worked up as described in example 3, to give 2-O—(N—BOC-glycyl)corosolic acid (200 mg).

A solution of 2-(N—BOC-glycyl)corosolic acid (200 mg) in CH$_2$Cl$_2$ (2 mL) was cooled to 0° C. and treated slowly with 2 mL of 1 N HCl in dioxane. After 30 min, the stirring was continued at rt for another 2 h. The reaction mixture was diluted with hexane (5 mL) and the precipitated solid was filtered, washed with hexane and dried to afford a white powder of 2-O-glycylcorosolic acid hydrochloride (190 mg), m.p. 268-272° C.; IR (KBr): 3432, 2979, 2926, 2859, 1749, 1690, 1461, 1243, 1050 cm$^{-1}$; $^1$H NMR (400 MHz, CD$_3$OD) δ 0.82-1.14 (7×CH$_3$), 2.2 (1H, brd, J=10.0 Hz), 3.80 (1H, brm, H-3), 3.88 (2H, s, OCOCH$_2$NH$_3$Cl), 4.66 (1H, d, J=9.9 Hz, H-2), 5.24 (1H, m, H-12), LCMS (positive ion mode): m/z 530 (M−Cl)$^+$.

Example 5

2-O-Alanylcorosolic acid hydrochloride (5): A mixture of corosolic acid (500 mg, 1.06 mmol), BOC protected alanine (240 mg, 1.23 mmol) and DMAP (75 mg) in dry dioxane (2 mL) at 0° C. was treated with DCC (327 mg, 1.59 mmol) under the conditions noted in example 4, obtained 2-O—(N—BOC-alanyl)corosolic acid (320 mg). This was deprotected as in example 4, to give 2-O-alanylcorosolic acid hydrochloride (250 mg) as white powder, m.p. 234-238° C.; IR (KBr): 3433, 2928, 2859, 1740, 1692, 1621, 1459, 1369, 1245, 1107, 1041 cm$^{-1}$; $^1$H NMR (400 MHz, DMSO-d$_6$) δ 0.57-1.35 (24H, m, 8×CH$_3$), 4.68-4.76 (1H, br s, —CH—N), 4.88-5.05 (1H, br s, H-3), 5.08-5.20 (1H, br s, H-12), 8.10-8.60 (3H, br s, NH$_3^+$); LCMS (positive ion mode): m/z 544 (M−Cl)$^+$.

Example 6

Methyl 2-O-(3,4,5-trimethoxycinnamoyl)corosolate (6): To a mixture of methyl corosolate (100 mg, 0.21 mmol), 3,4,5-trimethoxycinnamic acid (73 mg, 0.31 mmol) and DMAP (12 mg, 0.1 mmol) in CH$_2$Cl$_2$ (1.5 mL) cooled in an ice-water bath was added slowly DCC (85 mg, 0.41 mmol) in 0.5 mL of CH$_2$Cl$_2$. The mixture was allowed to reach ambient temperature and continued the stirring. After 2 h, the mixture was worked-up under the conditions noted in example 4, to finish methyl 2-O-(3,4,5-trimethoxycinnamoyl)corosolate (90 mg, 62%), m.p. 198-206° C.; IR (neat): 3460, 2927, 2854, 1717, 1632, 1583, 1457, 1263, 1098, 1024, 805 cm$^{-1}$; LCMS (positive ion mode): m/z 729 (M+Na)$^+$.

Example 7

2α,3β-Dihydroxyurs-12-en-28-oic acid 2,3-cyclicsulphate (7): To a mixture of corosolic acid (200 mg, 0.42 mmol)) and pyridine (0.34 mL, 4.2 mmol) in THF (1.5 mL) was slowly added thionyl chloride (40 μL, 4.2 mmol) and stirred at rt for 2 h. The reaction mixture was poured into 0.2N HCl (20 mL). The white precipitate was filtered, washed with water and dried under vacuum. This sulphite (100 mg) was dissolved in acetonitrile (1 mL), water (0.8 mL) and $CH_2Cl_2$ (1 mL) and treated with a solution of ruthenium trichloride monohydrate (100 μg) in acetonitrile (1 mL) followed by $NaIO_4$ (300 mg). The stirring was continued for 36 h. The mixture was poured into water and extracted with ethyl acetate. The organic layer was washed with brine, dried over $Na_2SO_4$ and evaporated. The residue (90 mg) was subjected to silica gel column chromatography using hexane-ethyl acetate (20%) as eluent to furnish cyclicsulphate derivative 7 (40 mg), m.p. 182-186° C.; IR (neat): 3431, 2926, 2871, 1693, 1459, 1386, 1211, 995, 959 cm$^{-1}$. LCMS (negative ion mode): m/z 533 (M–H)$^-$;

Example 8

Corosolamide (8): A mixture of diacetylcorosolic acid (300 mg) and thionyl chloride (2 mL) was refluxed for 1 h and the excess reagent was removed under reduced pressure to give acid chloride. This crude acid chloride in THF (1 mL) was added drop wise to a stirred solution of conc. ammonia (5 mL) at ice-cold temperature for 5 min and continued stirring at the same temperature for 2 h. The reaction mixture was poured into ice-cold water and extracted with ethyl acetate. The organic layer was washed with dil. $H_2SO_4$, water, brine and dried over sodium sulfate. The solution was filtered and the solvent evaporated to give diacetyl corosolamide (300 mg). A solution of diacetyl corosolamide (300 mg) and methanolic-potassium hydroxide (4%, 25 mL) was refluxed for 1 h. The solvent was evaporated under reduced pressure and diluted with ice-cold water and acidified with dil. $H_2SO_4$. The solution was extracted with ethyl acetate and the organic layer was washed with water, brine and dried over sodium sulfate. The residue obtained after evaporation of the solvent was chromatographed over silica gel column using chloroform-methanol (10%) as eluent to furnish corosolamide (200 mg, 67%), which was recrystallised from chloroform-hexane, m.p. 208-210° C.; IR (KBr): 3495, 2927, 2870, 1671, 1602, 1457, 1376, 1049, 959 cm$^{-1}$; $^1$H NMR (400 MHz, $CDCl_3$) δ 0.83 (3H, s, $CH_3$), 0.86 (3H, s, $CH_3$), 0.87 (3H, d, J=6.7 Hz, $CH_3$), 0.96 (3H, br s, $CH_3$), 1.00 (3H, s, $CH_3$), 1.04 (3H, s, $CH_3$), 1.11 (3H, S, $CH_3$), 3.00 (1H, d, J=9.4 Hz, H-3), 3.67-3.73 (1H, m, H-2), 5.32 (1H, br s, H-12), 5.85 (2H, br s, $CONH_2$); LCMS (negative ion mode): m/z 470 (M–H)$^-$.

Example 9

N-Phenylcorosolamide (9): Reaction of diacetylcorosolyl chloride (100 mg) with aniline (1 mL) in THF (10 mL) and triethyl amine (1 mL) under the conditions noted in example 8 gave N-phenylcorosolamide, which was crystallised from chloroform-methanol (60 mg, 61%), m.p. 168-174° C.; IR (KBr): 3408, 2927, 2868, 1652, 1599, 1529, 1502, 1442, 1312, 1235, 1048 cm$^{-1}$; $^1$H NMR (400 MHz, $CDCl_3$) δ 0.70 (3H, s, $CH_3$), 0.80 (3H, s, $CH_3$), 0.93-1.02 (12H, m, 2 methyl singlets merge with 2 methyl doublets), 1.14 (3H, s, $CH_3$), 3.00 (1H, d, J=7.76 Hz, H-3), 3.6-3.7 (1H, br. s, H-2), 5.45-5.50 (1H, br s, H-12), 7.07 (1H, br s, Ar—H), 7.28 (1H, br s, Ar—H), 7.44 (2H, br s, Ar—H), 7.67 (1H, br s, Ar—H); LCMS (positive ion mode): m/z 548 (M+H)$^+$.

Example 10

N-(2-Aminoethyl)corosolamide (10): Reaction of diacetylcorosolyl chloride (200 mg) with ethylene diamine (1.0 g) in THF (10 mL) and work-up under the conditions noted in example 8 furnished N-(2-aminoethyl)corosolamide (110 mg, 60%), m.p. 118-120° C.; IR (KBr): 3403, 2926, 1633, 1527, 1454, 1383, 1048 cm$^{-1}$; $^1$H NMR (400 MHz, DMSO-$d_6$) δ 0.69 (3H, s, $CH_3$), 0.72 (3H, s, $CH_3$), 0.84 (3H, d, J=6.0 Hz, $CH_3$), 0.92-0.94 (9H, 2 br s, 2 methyl singlets and a methyl doublet), 0.99 (2H, d, J=7.2 Hz, —NCO—$CH_2$—), 1.05 (3H, s, $CH_3$), 2.17 (1H, d, J=11.2 Hz, H-18), 2.57 (2H, q, J=7.0 Hz, $NH_2$—$CH_2$), 2.70 (2H, t, J=6.7 Hz, $NH_2$—$CH_2$), 2.75 (1H, d, J=9.2 Hz, H-3), 4.3-4.4 (1H, m, H-2), 5.23 (1H, br s, H-12); LCMS (positive ion mode): m/z 515 (M+H)$^+$.

Example 11

N-(Corosolyl)piperazine (11): Reaction of diacetylcorosolyl chloride (100 mg) with piperazine (200 mg) in THF (10 mL) and triethyl amine (2 mL) and work-up under the conditions noted in example 8 gave N-(corosolyl)piperazine, which was crystallised from chloroform-hexane (50 mg, 52%), m.p. 226-230° C.; IR (KBr): 3434, 2924, 2868, 1628, 1455, 1226, 1049 cm$^{-1}$; $^1$H NMR (400 MHz, $CDCl_3$) δ 0.76 (3H, s, $CH_3$), 0.83 (3H, s, $CH_3$), 0.87 (3H, d, J=6.3 Hz, $CH_3$), 0.94 (3H, d, J=6.2 Hz, $CH_3$), 0.99 (3H, s, $CH_3$), 1.03 (3H, s, $CH_3$), 1.08 (3H, s, $CH_3$), 2.44 (1H, d, J=8.6 Hz, H-18), 2.83 (4H, s, N—$CH_2$), 3.00 (1H, d, J=9.5 Hz, H-3), 3.58 (4H, d, J=3.4 Hz, N—$CH_2$), 3.66-3.72 (1H, m, H-2), 5.23 (1H, br s, H-12); LCMS (positive ion mode): m/z 541 (M+H)$^+$.

Example 12

N-(2-Hydroxyethyl)corosolamide (12): Reaction of diacetylcorosolyl chloride (100 mg) with 2-aminoethanol (1 mL) in THF (10 mL) and triethyl amine (1 mL) under the conditions noted in example 8 gave N-(2-hydroxyethyl)corosolamide, which was crystallised from chloroform-hexane to obtain 12 (43 mg, 47%), m.p. 152-158° C.; IR (KBr): 3408, 2963, 2926, 2856, 1632, 1529, 1455, 1262, 1094, 1026, 802 cm$^{-1}$; $^1$H NMR (400 MHz, $CDCl_3$) δ 0.81 (3H, s, $CH_3$), 0.83 (3H, s, $CH_3$), 0.87 (3H, d, J=6.2 Hz, $CH_3$), 0.96 (3H, br s, $CH_3$), 1.00 (3H, s, $CH_3$), 1.04 (3H, s, $CH_3$), 1.11 (3H, s, $CH_3$), 2.98 (1H, br s), 3.00 (1H, d, J=9.3 Hz, H-3), 3.21-3.26 (1H, m), 3.44-3.49 (1H, m, H-2), 3.68 (3H, br s, N—$CH_2CH_2$—), 5.34 (1H, s, H-12), 6.34 (1H, br s); LCMS (negative ion mode): m/z 514 (M–H)$^-$.

Example 13

Methyl corosolate (13): A mixture of corosolic acid (2.0 g, 4.34 mmol), iodomethane (1 mL, 16 mmol), potassium carbonate (4.5 g, 32.6 mmol) and acetone (60 mL) was stirred at rt for 16 h. After completion of the reaction, the solids were filtered off and the solvent was evaporated under reduced pressure. The residue was chromatographed over silica gel column using chloroform-methanol (10%) as eluent to furnish methyl corosolate (1.7 g, 83%), which was recrystallised from chloroform-hexane, m.p. 208-210° C.; IR (KBr): 3432, 2946, 2872, 1728, 1455, 1230, 1197, 1049 cm$^{-1}$; $^1$H NMR (400 MHz, $CDCl_3$) δ 0.75 (3H, s, $CH_3$), 0.83 (3H, s, $CH_3$), 0.85 (3H, d, J=6.5 Hz, $CH_3$), 0.94 (3H, d, J=5.7 Hz, $CH_3$), 0.99 (3H, s, $CH_3$), 1.03 (3H, s, $CH_3$), 1.08 (3H, s, $CH_3$), 2.23 (1H, d, J=11.0 Hz, H-18), 3.0 (1H, d, J=8.4 Hz, H-3), 3.60 (3H, s, —$COOCH_3$), 3.62-3.71 (1H, m, H-2), 5.25 (1H, t, J=3.4 Hz, H-12); LCMS (negative ion mode): m/z 485 (M–H)$^-$.

Example 14

Methyl diacetylcorosolate (14): Reaction of diacetylcorosolic acid (500 mg, 0.9 mmol) with iodomethane (0.25 mL, 4.0 mmol), potassium carbonate (1.0 g, 7.2 mmol) and acetone (25 mL) under the conditions noted in example 13 gave methyl diacetylcorosolate (0.4 g, 78%), which was crystallised from aq. methanol to obtain 14, m.p. 138-140° C.; IR (KBr): 2943, 1742, 1243, 1036, 964 cm$^{-1}$; $^1$H NMR (400 MHz, CDCl$_3$) δ 0.75 (3H, s), 0.85 (3H, d, J=6.4 Hz), 0.90 (3H, s), 0.91 (3H, s), 0.94 (3H, d, J=5.9 Hz), 1.07 (6H, s), 1.97 (3H, s), 2.05 (3H, s), 2.23 (1H, d, J=11.4 Hz, H-18), 3.60 (3H, s), 4.75 (1H, d, J=10.3 Hz, H-3), 5.07-5.14 (1H, m, H-2), 5.23-5.24 (1H, m. H-12); LCMS (positive mode): 594 (M+1)$^+$.

Example 15

Methyl 11-ketocorosolate (15): Methyl corosolate (400 mg) was acetylated using pyridine (0.5 mL) and acetic anhydride (0.5 mL) under the conditions noted in example 2 to furnish methyl diacetylcorosolate (450 mg), which was dissolved in 1,4-dioxane (16 mL) and treated with N-bromosuccinimide (472 mg), water (1.6 mL) and calcium carbonate (472 mg). The reaction mixture was subjected to vigorous stirring for 3 h, and then filtered. The mother liquor was poured into cold water and extracted with ethyl acetate. The organic layer was washed with brine, dried over sodium sulfate and evaporated. The residue (360 mg) in methanol (2 mL) was added 8N KOH solution (1 mL) and stirred at 65° C. for 1 h, then poured into ice cold water, acidified with 2N HCl and extracted with ethyl acetate. The organic layer was washed with brine, dried over sodium sulfate and evaporated. The residue (340 mg) was purified over silica gel column using hexane-ethyl acetate (25%) as eluent to furnish methyl 11-ketocorosolate (240 mg), m.p. 101-105° C.; IR (neat): 3416, 2926, 2858, 1728, 1659, 1457, 1388, 1201, 1048 cm$^{-1}$; $^1$H NMR (400 MHz, CDCl$_3$) δ 0.84 (3H, s, CH$_3$), 0.87 (3H, d, J=6.5 Hz, CH$_3$), 0.91 (3H, s, CH$_3$), 0.97 (3H, d, J=6.3 Hz, CH$_3$), 1.05 (3H, s, CH$_3$), 1.19 (3H, s, CH$_3$), 1.30 (3H, s, CH$_3$), 2.35 (1H, s), 2.42 (1H, d, J=10.9 Hz), 3.02 (1H, d, J=9.5 Hz), 3.16 (1H, dd, J=12.6 & 4.3 Hz), 3.61 (3H, s, CH$_3$), 3.77 (1H, m, H-2), 5.61 (1H, s, H-12); LCMS (positive ion mode): m/z 501 (M+H)$^+$.

Example 16

Methyl diacetyl-11-ketocorosolate (16): Reaction of methyl diacetylcorosolate, (500 mg, 0.9 mmol) in 1,4-dioxane (20 mL) with N-bromosuccinimide (0.75 g, 4.2 mmol) and calcium carbonate (0.75 g, 7.5 mmol) in water (2 mL) under the conditions noted in example 15 gave methyl diacetyl-11-ketocorosolate (300 mg, 59%), which was crystallized from aq. methanol to obtain 16, m.p. 264-266° C.; IR (KBr): 2952, 1734, 1660, 1241, 1038, 985 cm$^{-1}$; $^1$H NMR (400 MHz, CDCl$_3$) δ 0.86 (3H, d, J=6.4 Hz), 0.89 (3H, s), 0.91 (3H, s), 0.93 (3H, s), 0.97 (3H, d, J=6.3 Hz), 1.25 (3H, s), 1.29 (3H, s), 1.95 (3H, s), 2.04 (3H, s), 3.18 (1H, dd, J=12.8, 4.6 Hz, H-18), 3.60 (3H, s), 4.72 (1H, d, J=10.3 Hz, H-3), 5.20-5.26 (1H, m, H-2), 5.61 (1H, s, H-12); LCMS (positive ion mode): m/z 608 (M+H)$^+$.

Example 17

11-Ketocorosolic acid (17): A mixture of corosolic acid (400 mg, 0.85 mmol), pyridine (0.4 mL, 5.1 mmol) and acetic anhydride (1.5 mL, 15.2 mmol) was stirred at rt for 6 h. To the cooled reaction mixture after diluting with acetic acid (1.5 mL) and acetic anhydride (2 mL) was added chromium trioxide (254 mg) and stirred for 5 h. The reaction mixture was poured into ice-cold water and the precipitated solid was filtered and washed with water. The solid in methanol (4 mL) was treated with 8N KOH (2 mL) and stirred at rt for 14 h and then the mixture was filtered through celite. The mother liquor was poured into ice water, acidified and extracted with ethyl acetate. The organic layer was washed with brine, dried over sodium sulphate and evaporated. The residue (390 mg) was purified over silica gel column using hexane-ethyl acetate (30%) as eluent to furnish 11-ketocorosolic acid (60 mg), m.p. 238-242° C.; IR (neat): 3417, 2927, 2857, 1692, 1659, 1460, 1386, 1051, 974 cm$^{-1}$; LCMS (negative ion mode): m/z 485 (M-H)$^-$.

Example 18

Diacetyl-11-ketocorosolic acid (18): Reaction of diacetyl corosolic acid (500 mg, 0.9 mmol) in dichloroethane (2 mL), acetic acid (2 mL) and water (1 mL) with a solution of chromium trioxide (1.5 g, 15 mmol), acetic acid (2 mL) and water (2 mL) under the conditions noted in example 17 gave diacetyl-11-ketocorosolic acid (200 mg, 39%), which was crystallized from chloroform-hexane to obtain 18, m.p. 318-320° C.; IR (KBr): 3184, 2975, 1742, 1641, 1253, 1036 cm$^{-1}$; $^1$H NMR (400 MHz, CDCl$_3$) δ 0.86 (3H, d, J=6.4 Hz), 0.90 (3H, s), 0.91 (6H, s), 0.98 (3H, d, J=6.2 Hz), 1.26 (3H, s), 1.30 (3H, s), 1.95 (3H, s, —OCOCH$_3$), 2.05 (3H, s, —OCOCH$_3$), 3.18 (1H, dd, J=12.7, 3.2 Hz, H-18), 4.72 (1H, d, J=10.3 Hz, H-3), 5.19-5.26 (1H, m, H-2), 5.61 (1H, s, H-12); LCMS (negative mode): 569 (M-H)$^-$.

Example 19

2α,3β-Dihydroxyurs-12-en-11-one-28-oic acid 2,3-cyclicsulphate (19): To a mixture of corosolic acid-2,3-sulfite (1.1 g, 2.12 mmol), dichloromethane (7 mL) and acetonitrile (4 mL) was added ruthenium chloride (2 mg) in acetonitrile (2 mL), followed by sodium periodate (1.5 g). After stirring the mixture at rt for 2 h, an additional amount (0.5 g) of sodium periodate was added and after 2 h of stirring, the reaction mixture was worked up under the conditions noted in example 7 to give 2,3-cyclicsulphate derivative 19 (600 mg), m.p. 210-216° C.; IR (neat): 3429, 2924, 2356, 1705, 1658, 1618, 1380, 1206 cm$^{-1}$; $^1$H NMR (400 MHz, DMSO-d$_6$) δ 0.82 (3H, d, J=6.3 Hz, CH$_3$), 0.90 (3H, s, CH$_3$), 0.94 (3H, s, CH$_3$), 0.95 (3H, d, J=6.4 Hz, CH$_3$), 1.07 (3H, s, CH$_3$), 1.20 (3H, s, CH$_3$), 1.31 (3H, s, CH$_3$), 3.20 (1H, dd, J=11.6 & 4.2 Hz, H-18), 4.63 (1H, d, J=10.4 Hz, H-3), 5.20-5.30 (1H, m, H-2), 5.44 (1H, s, H-12); LCMS (negative ion mode): m/z 547 (M-H)$^-$.

Example 20

11-Ketocorosolamide (20): Diacetyl-11-ketocorosolyl chloride (prepared from the 11-ketoacid, 150 mg and thionyl chloride 2 mL) was dissolved in THF (2 mL) and the solution was added dropwise to a stirred solution of conc. ammonia (5 mL) at ice cold temperature for 5 min and the solution was stirred at the same temperature for 2 h. The reaction mixture was worked up as described in example 8 to furnish 11-ketocorosolamide (40 mg, 31%), m.p. 220-222° C.; IR (KBr): 3427, 2970, 2930, 2871, 1659, 1459, 1384, 1200, 1048, 971 cm$^{-1}$; $^1$H NMR (400 MHz, DMSO-d$_6$) δ 0.72 (3H, s, CH$_3$), 0.82 (3H, d, J=6.3 Hz, CH$_3$), 0.89 (3H, s, CH$_3$), 0.93 (3H, s, CH$_3$), 0.95 (3H, d, J=6.3 Hz, CH$_3$), 1.08 (3H, s, CH$_3$), 1.27 (3H, s, CH$_3$), 2.32 (1H, s), 2.36 (1H, d, J=11.1 Hz, H-18), 2.75 (1H, dd, J=12.7 & 4.2 Hz), 2.86 (1H, dd, J=12.7 & 4.2 Hz), 3.48 (1H, br s, H-2), 4.23 (1H, d, J=3.8 Hz), 4.34 (1H, d, J=3.8 Hz), 5.47 (1H, s, H-12), 6.83 (1H, s, OH), 6.97 (1H, s, OH); LCMS (positive ion mode): m/z 486 (M+H)$^+$.

Example 21

11-Hydroxycorosolamide (21): To a magnetically stirred ice cold (10-15° C.) solution of 11-ketocorosolamide (50 mg, 0.10 mmol) in ethanol (10 mL) was added sodium borohydride (200 mg, 5.26 mmol) and the solution was slowly brought to rt and stirred for 14 h. After completion of the reaction, the mixture was poured into ice-cold water and acidified with dil HCl. The solution was extracted with ethyl acetate and the organic layer was washed with water, brine and dried over sodium sulfate. The residue obtained after evaporation of the solvent was chromatographed over silica gel column using chloroform-methanol (95:5) as eluent to give 11-hydroxycorosolamide (20 mg, 40%), which was crystallised from chloroform-methanol, m.p. 196-198° C.; IR (KBr): 3432, 2929, 1659, 1600, 1383, 1048, 968 cm$^{-1}$; $^1$H NMR (400 MHz, DMSO-d$_6$) δ 0.73 (3H, s, CH$_3$), 0.77 (3H, s, CH$_3$), 0.90-0.94 (9H, m, 2 methyl doublets and a methyl singlet), 1.02 (3H, s, CH$_3$), 1.11 (3H, s, CH$_3$), 2.11 (1H, d, J=10.7 Hz, H-18), 2.42-2.46 (1H, m), 2.73 (1H, dd, J=9.1 & 3.7 Hz, H-3), 3.42 (1H, m, H-2), 4.01-4.03 (2H, m, H-11 & 11-OH), 4.15 (1H, br s, NH$_2$), 4.28 (1H, br s, NH$_2$), 5.17 (1H, s, H-12), 6.68 (1H, s, OH), 6.73 (1H, s, OH); LCMS (negative ion mode): m/z 486 (M–H)$^-$.

Example 22

Methyl 11-hydroxycorosolate (22): To a magnetically stirred ice cold (10-15° C.) solution of methyl 11-ketocorosolate (360 mg, 0.72 mmol) in ethanol (40 mL) was added sodium borohydride (1.0 g, 26 mmol) and the solution was slowly brought to rt and stirred for 14 h. After completion of the reaction, the mixture was worked up as described in example 21 to give methyl 11-hydroxycorosolate (32 mg), m.p. 148-152° C.; IR (Neat): 3416, 2927, 2872, 1719, 1648, 1455, 1388, 1220, 1146, 1047, 999, 960, 770 cm$^{-1}$; $^1$H NMR (400 MHz, CDCl$_3$) δ 0.86 (6H, s, 2×CH$_3$), 0.95 (3H, d, J=6.0 Hz, CH$_3$), 1.01-1.03 (12H, 3 methyl singlets and a methyl doublet), 2.31 (1H, d, J=11.3 Hz, H-18), 2.44 (1H, dd, J=12.0 & 4.2 Hz), 3.02 (1H, d, J=9.3 Hz, H-3), 3.80-3.83 (1H, m, H-2), 4.39 (1H, m, H-11), 5.35 (1H, d, J=3.8 Hz, H-12); LCMS (negative ion mode): m/z 501 (M–H)$^-$.

Example 23

Corosolinol (23): To an ice cold dispersion of lithium aluminum hydride (97 mg) in THF (3 mL) was slowly added methyl corosolate (500 mg) in THF (1 mL) and stirred for 2 h. The reaction mixture was diluted with ethyl acetate (3 mL) and poured into ice water. The mixture was acidified with 2 N HCl and extracted with ethyl acetate (50 mL). The organic layer was washed with brine, dried over Na$_2$SO$_4$ and evaporated. The residue (400 mg) was chromatographed over silica gel column using hexane-ethyl acetate (80:20) as eluents to yield corosolinol (220 mg), m.p. 140-146° C.; IR (neat): 3392, 2926, 2867, 1619, 1456, 1388, 1047, 1024, 760 cm$^{-1}$; $^1$H NMR (400 MHz, CDCl$_3$) δ 0.81 (3H, d, J=5.4 Hz, CH$_3$), 0.84 (3H, s, CH$_3$), 0.94 (3H, d, J=5.3 Hz, CH$_3$), 0.99 (3H, s, CH$_3$), 1.03 (3H, s, CH$_3$), 1.04 (3H, s, CH$_3$), 1.11 (3H, s, CH$_3$), 2.03 (1H, dd, J=12.3 & 4.5 Hz), 3.01 (1H, d, 3=9.6 Hz), 3.19 (1H, d, J=11.0 Hz), 3.53 (1H, d, J=11.0 Hz), 3.70 (1H, m, H-2), 5.15 (1H, t, J=3.4 Hz, H-12); LCMS (negative ion mode): m/z 457 (M–H)$^-$.

Example 24

Corosolinal (24): To a cooled solution of Dess-Martin Periodinane (23 mg) in CH$_2$Cl$_2$ (2 mL) was slowly added corosolinol (20 mg) dissolved in CH$_2$Cl$_2$ (2 mL) and the solution was allowed to ambient temperature and continued the stirring for 2 h. The mixture was diluted with Et$_2$O (20 mL) and poured into an ice-cold mixture of Na$_2$S$_2$O$_3$.5H$_2$O (90 mg) in saturated aqueous NaHCO$_3$ (5 mL). The layers were separated and the organic layer was washed with saturated aqueous NaHCO$_3$ (10 mL), water (20 mL), brine (20 mL) and dried over MgSO$_4$. The solution was filtered and evaporated to give corosolinal (15 mg) as a colorless oil. IR (neat): 3433, 2925, 2855, 1721, 1451, 1387, 1094 cm$^{-1}$; LCMS (negative ion mode): m/z 455 (M–H)$^-$.

Example 25

Corosolyl tri-O-methylgallate (25): A mixture of tri-O-methylgallic acid (200 mg, 0.9 mmol) and SOCl$_2$ (0.5 mL) was refluxed for 0.5 h. The excess reagent was removed under high vacuum and the residue in CH$_2$Cl$_2$ (1 mL) was added to a mixture of corosolic acid (200 mg, 0.42 mmol) and DMAP (30 mg) in dioxane (5 mL). The reaction mixture was stirred at rt for 2 h and then poured into ice-cold water. The mixture was extracted with ethyl acetate (60 mL) and the organic layer was washed with 0.1 N HCl (40 mL), water (40 mL), brine and dried over Na$_2$SO$_4$. The residue obtained after evaporation of the solvent was chromatographed over silica gel column using hexane-ethyl acetate (85:15) as eluent to yield corosolyl tri-O-methylgallate (25) as a white solid (75 mg), m.p. 158-162° C.; IR (KBr): 3439, 2930, 2853, 1793, 1728, 1627, 1584, 1460, 1336, 1233, 1129, 1019 cm$^{-1}$; $^1$H NMR (400 MHz, CDCl$_3$) δ 0.83 (3H, s, CH$_3$), 0.89 (3H, s, CH$_3$), 0.99 (3H, s, CH$_3$), 1.04 (3H, s, CH$_3$), 1.13 (3H, s, CH$_3$), 1.25 (3H, s, CH$_3$), 2.35 (1H, s), 2.30 (1H, d, J=11.0 Hz), 3.00 (1H, d, J=9.3 Hz), 3.70 (1H, brm), 3.90 (9H, s, 3×CH$_3$), 5.37 (1H, s, H-12), 7.28 (2H, s, Ar—H); LCMS (positive ion mode): m/z 689 (M+Na)$^+$.

Example 26

2α,3β-Dihydroxyurs-12-en-11,28-olide (26): To a solution of corosolic acid (200 mg) in dioxane (6 mL) and water (0.6 mL) was added NBS (188 mg) and CaCO$_3$ and the mixture stirred at rt for 4 h. The mixture was poured in to ice water (30 mL) and extracted with ethyl acetate (2×30 mL). The combined organic layer was washed with water (30 mL) followed by brine and dried over Na$_2$SO$_4$. The solvent was evaporated and the residue was subjected to silica gel column chromatography using hexane and ethyl acetate mixtures as eluents to obtain the lactone, 26 as a semisolid (60 mg); IR (neat): 3339, 2925, 2854, 1763, 1465 1261, 1021 cm$^{-1}$; $^1$H NMR (400 MHz, CDCl$_3$) δ 0.75-1.25 (7×CH$_3$), 3.02 (1H, br s), 3.75 (1H, brm), 5.56 (1H, brd, J=8.2 Hz), 5.98 (1H, brd, J=8.2 Hz); LCMS (negative ion mode): m/z 469 (M–H)$^-$.

Hypoglycemic activity: Hypoglycemic activity was tested by the inhibition of sucrose-induced raise in serum glucose levels (SGL), by the test substances in Albino wistar rats. The procedure involves fasting the rats for overnight at ad libitum water, numbered weighed and randomly divided into groups of six animals each. Prior to treatment blood samples were drawn from sinus orbital plexus of all animals using heparin coated glass capillaries under mild ether anesthesia. The blood samples were tested for serum glucose levels using enzymatic GOD/POD method. Optical densities were measured at 500 nm, SGL was calculated as follows. SGL=(test OD/Standard OD)×100 and the results were expressed in mg/dL. All the groups were treated orally with corresponding test substances, standard, vehicle (5% gum acacia). After 30 minutes, all animals were given 20 mL/kg of 20% sucrose solution orally using gastric tube. One hour after treatment, blood samples were drawn again under mild ether anesthesia and tested for serum glucose levels in a same procedure as described above for initial serum glucose estimation. The data was subjected to statistical treatment using t-test and inhibitory rate was calculated by comparing mean increase in serum glucose levels of control and treated groups.

5-Lipoxygenase activity: The corosolic acid analogs were screened for their 5-Lipoxygenase inhibitory potential using colorimetric method. The assay mixture contained 50 mM phosphate buffer pH 6.3, 5-Lipoxygenase, various concentrations of test substances in dimethyl sulphoxide and linoleic acid in a total volume of 0.5 mL, after 5 min incubation of above reaction mixture, 0.5 mL ferric xylenol orange reagent was added and OD was measured after two minutes at 585 nm using spectrophotometer. Controls were run along with test in a similar manner except using vehicle instead of test substance solution. Percent inhibition was calculated by comparing absorbance of test solution with that of control.

Brine shrimp lethality: Brine shrimp (*Artemia salina*) nauplii were hatched using brine shrimp eggs in a conical shaped vessel (1 L), filled with sterile artificial sea water (prepared using sea salt 38 g/L and adjusted to pH 8.5 using 1 N NaOH) under constant aeration for 48 h. After hatching, 10 nauplii were drawn through a pepette and placed in each vial containing 4.5 mL brine solution and added various concentrations of drug solutions and volume was made upto 5 mL using brine solution and maintained at 37° C. for 24 h under the light of incandescent lamps and surviving larvae were counted. Each experiment was conducted along with control (vehicle treated), at various concentrations of the test substance in each set that contains 6 tubes and the average results are reported. The percentage lethality was determined by comparing the mean mortal larvae of test and control tubes. $LC_{50}$ values were obtained from the plot of concentration (μg) vs. percentage lethality. Podophyllotoxin was used as a positive control.

The corosolic acid analogs of this invention are found to show better hypoglycemic activity (Table 1; hypoglycemic activity is expressed in serum glucose level inhibitory rate values; higher the inhibitory rate value, higher is the activity) than the corosolic acid.

The corosolic acid analogs of this invention are found to show good 5-lipoxygenase activity (Table 2; 5-lipoxygenase activity is expressed in % of inhibition at 100 μM and 250 μM; higher the % inhibitory values, higher is the activity).

The corosolic acid analogs of this invention are found to show significant brine shrimp lethality (Table 3; brine shrimp lethality is expressed in $LC_{50}$ at μM concentration; lower the $LC_{50}$ value, higher is the activity).

TABLE I

Hypoglycemic activity

| S. No | Comp. No. | Oral dose in mg/Kg | SGL (mean ± SE) | Inhibitory rate | t-value |
|---|---|---|---|---|---|
| 1 | Control | 5% GA | 134.56 ± 1.47 | | |
| 2 | Corosolic acid | 1 mg | 121.43 ± 6.27 | 9.78 | 2.04 |
| 3 | 1 | 1 mg | 109.54 ± 2.80 | 32.75 | 13.83 |
| 4 | 3 | 1 mg | 115.86 ± 3.77 | 13.9 | 4.62 |
| 5 | 4 | 1 mg | 119.23 ± 9.58 | 26.8 | 4.39 |
| 6 | 5 | 1 mg | 113.49 ± 4.11 | 22.39 | 7.68 |
| 7 | 6 | 1 mg | 114.15 ± 6.62 | 21.94 | 4.78 |
| 8 | 8 | 1 mg | 110.14 ± 3.18 | 18.15 | 6.97 |
| 9 | 9 | 1 mg | 117.97 ± 0.37 | 27.58 | 16.78 |
| 10 | 10 | 1 mg | 113.57 ± 3.80 | 30.28 | 10.64 |

TABLE I-continued

Hypoglycemic activity

| S. No | Comp. No. | Oral dose in mg/Kg | SGL (mean ± SE) | Inhibitory rate | t-value |
|---|---|---|---|---|---|
| 11 | 11 | 1 mg | 107.88 ± 4.61 | 19.83 | 5.51 |
| 12 | 12 | 1 mg | 103.49 ± 7.12 | 36.47 | 7.82 |
| 13 | 13 | 1 mg | 118.94 ± 8.61 | 11.6 | 1.79 |
| 14 | 15 | 1 mg | 120.79 ± 4.85 | 17.4 | 5.11 |
| 15 | 17 | 1 mg | 120.90 ± 9.66 | 25.78 | 4.19 |
| 16 | 19 | 1 mg | 129.16 ± 4.66 | 11.67 | 3.56 |
| 17 | 20 | 1 mg | 142.81 ± 7.30 | 12.33 | 2.58 |
| 18 | 21 | 1 mg | 121.57 ± 2.62 | 25.37 | 11.08 |
| 19 | 23 | 1 mg | 113.06 ± 2.61 | 30.59 | 13.40 |
| 20 | 25 | 1 mg | 131.84 ± 7.77 | 9.84 | 1.83 |
| 21 | 26 | 1 mg | 136.03 ± 4.43 | 6.97 | 2.23 |

TABLE 2

5-Lipoxygenase inhibitory activity

| | | % inhibition of 5-Lox activity at various concentrations | |
|---|---|---|---|
| S. No | Comp. No. | 100 μM | 250 μM |
| 1 | Corosolic acid | 13.48 | 29.26 |
| 2 | 1 | 15.47 | 24.05 |
| 3 | 2 | 20.08 | 44.54 |
| 4 | 3 | 28.54 | 53.19 |
| 5 | 4 | 17.04 | 27.83 |
| 6 | 5 | 29.14 | 67.03 |
| 7 | 6 | — | 13.47 |
| 8 | 7 | — | 16.90 |
| 9 | 8 | 26.13 | 51.29 |
| 10 | 9 | 8.16 | 21.77 |
| 11 | 10 | 21.74 | 40.87 |
| 12 | 11 | 35.42 | 64.99 |
| 13 | 12 | 17.74 | 32.96 |
| 14 | 13 | 17.3 | 40.04 |
| 15 | 14 | — | 1.9 |
| 16 | 15 | — | 25.09 |
| 17 | 16 | — | 3.82 |
| 18 | 19 | — | 11.81 |
| 19 | 20 | 18.57 | 42.79 |
| 20 | 21 | 25.57 | 50.83 |
| 21 | 22 | 24.56 | 49.40 |
| 22 | 23 | 2.91 | 19.63 |
| 23 | 25 | — | 38.83 |
| 24 | 26 | — | 10.47 |
| 25 | AKBA | 17.45 | 25.3 |
| 26 | NDGA | 70.4 | 91.55 |

AKBA: Acetyl ketoboswellic acid
NDGA: Nordihydroguaiaretic acid

TABLE 3

Brine Shrimp Lethality Test

| S. No | Compound No. | $LC_{50}$ (μM) |
|---|---|---|
| 1 | Corosolic acid | 3.0 |
| 2 | 1 | 9.7 |
| 3 | 2 | 1.8 |
| 4 | 3 | 86.6 |
| 5 | 4 | 3.9 |
| 6 | 5 | 3.4 |
| 7 | 6 | >200 |
| 8 | 7 | 15.0 |
| 9 | 8 | 29.0 |
| 10 | 9 | >100 |
| 11 | 10 | 97.2 |

TABLE 3-continued

Brine Shrimp Lethality Test

| S. No | Compound No. | LC$_{50}$ (μM) |
|---|---|---|
| 12 | 11 | 9.2 |
| 13 | 12 | >100 |
| 14 | 13 | 10.2 |
| 15 | 14 | 42.1 |
| 16 | 15 | 40.9 |
| 17 | 16 | 82.3 |
| 18 | 18 | 87.7 |
| 19 | 19 | >100 |
| 20 | 20 | >100 |
| 21 | 21 | >100 |
| 22 | 22 | 19.9 |
| 23 | 23 | 30.7 |
| 24 | 25 | >200 |
| 25 | 26 | 87.0 |
| 26 | podophyllotoxin | 7.7 |

The invention claimed is:

1. Corosolic acid analogs represented by the formula I,

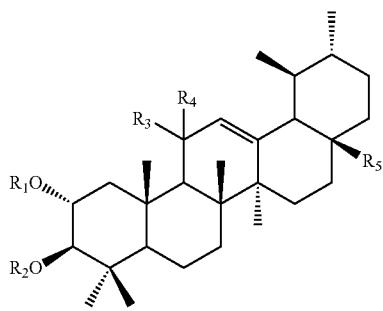

I wherein $R_1$, $R_2$, $R_3$, $R_4$ and $R_5$ are as indicated below in each of said analogs:

$R_1$=COC$_5$H$_4$N, $R_2$=$R_3$=$R_4$=H, $R_5$=COOH;
$R_1$=$R_2$=$R_3$=$R_4$=H, $R_5$=CONHC$_6$H$_5$;
$R_1$=$R_2$=$R_3$=$R_4$=H, $R_5$=CONHCH$_2$CH$_2$NH$_2$;
$R_1$=$R_2$=$R_3$=$R_4$=H, $R_5$=CON(CH$_2$CH$_2$)$_2$NH;
$R_1$=$R_2$=$R_3$=$R_4$=H, $R_5$=CONHCH$_2$CH$_2$OH;
and $R_1$=$R_2$=$R_3$=$R_4$=H, $R_5$=CHO.

2. The corosolic acid analog of the formula I, as claimed in claim 1, wherein $R_1$ is COC$_5$H$_4$N, $R_2$, $R_3$ and $R_4$ are H, and $R_5$ is COOH, which is 2-O-nicotinoylcorosolic acid.

3. The corosolic acid analog of the formula I, as claimed in claim 1, wherein $R_1$, $R_2$, $R_3$ and $R_4$ are H, and $R_5$ is CONHPh, which is N-phenylcorosolamide.

4. The corosolic acid analog of the formula I, as claimed in claim 1, wherein $R_1$, $R_2$, $R_3$ and $R_4$ are H, and $R_5$ is CONHCH$_2$CH$_2$NH$_2$, which is N-(2-aminoethyl)corosolamide.

5. The corosolic acid analog of the formula I, as claimed in claim 1, wherein $R_1$, $R_2$, $R_3$ and $R_4$ are H, and $R_5$ is CON(CH$_2$CH$_2$)$_2$NH, which is N-corosolylpiperazine.

6. The corosolic acid analog of the formula I, as claimed in claim 1, wherein $R_1$, $R_2$, $R_3$ and $R_4$ are H, and $R_5$ is CONHCH$_2$CH$_2$OH, which is N-(2-hydroxyethyl)corosolamide.

7. The corosolic acid analog of the formula I, a claimed in claim 1, wherein $R_1$, $R_2$, $R_3$ and $R_4$ are H, and $R_5$ is CHO, which is corosolinal.

8. A pharmaceutical composition containing at least one corosolic acid analog as claimed in claim 1 and a pharmaceutically acceptable carrier.

9. The pharmaceutical composition as claimed in claim 8 wherein said carrier is an aqueous or non-aqueous carrier.

* * * * *